United States Patent
Blackledge et al.

(10) Patent No.: US 6,520,978 B1
(45) Date of Patent: Feb. 18, 2003

(54) EMBOLI FILTER

(75) Inventors: Victor R. Blackledge, Cologne, MN (US); Charles H. Whatley, Jr., Louisville, KY (US); Benjamin E. Morris, Louisville, KY (US); Todd A. Hall, Goshen, KY (US); William A. Reuss, Jr., Louisville, KY (US)

(73) Assignee: IntraTherapeutics, Inc., St. Paul, MN (US)

( * ) Notice: Subject to any disclaimer, the term of this patent is extended or adjusted under 35 U.S.C. 154(b) by 0 days.

(21) Appl. No.: 09/570,659

(22) Filed: May 15, 2000

(51) Int. Cl.⁷ .............................................. A61M 29/00
(52) U.S. Cl. ..................................................... 606/200
(58) Field of Search ................................ 606/200, 159, 606/194, 191, 108, 198, 113, 114, 127

(56) References Cited

U.S. PATENT DOCUMENTS

| | | | |
|---|---|---|---|
| 5,695,519 A | | 12/1997 | Summers et al. |
| 6,059,814 A | | 5/2000 | Ladd |
| 6,146,396 A | * | 11/2000 | Konya et al. ................ 606/159 |
| 6,152,946 A | * | 11/2000 | Broome et al. ............. 606/200 |
| 6,171,327 B1 | * | 1/2001 | Daniel et al. ................ 606/159 |
| 6,299,636 B1 | * | 10/2001 | Schmitt et al. ............... 600/36 |
| 6,346,116 B1 | * | 2/2002 | Brooks et al. ............... 606/159 |

FOREIGN PATENT DOCUMENTS

| | | |
|---|---|---|
| WO | WO 99/44542 | 9/1999 |
| WO | WO 00/16705 | 3/2000 |
| WO | WO 01/08743 A1 | 2/2001 |

\* cited by examiner

Primary Examiner—Michael J. Milano
Assistant Examiner—(Jackie) Tan-Uyen T. Ho
(74) Attorney, Agent, or Firm—Merchant & Gould P.C.

(57) ABSTRACT

An emboli filter for deployment in a body lumen to capture emboli entrained in a fluid flowing through the lumen includes a flexible elongated member sized to be passed through the lumen. A filter media is carried on and substantially surrounding the elongated member. The filter media has a first end secured to the elongated member adjacent the distal end. A second end of the filter media has a periphery movable toward and away from the elongated member. Opposing internal surfaces of the filter media define a volume into which emboli may flow through the second end when the periphery is moved away from the elongated member. The emboli are trapped within the volume when the periphery is moved toward the elongated member. An actuator moves the periphery toward and way from the elongated member. The actuator includes a plurality of elastic loops. The loops are biased to an open loop configuration with the loops urging the periphery away from the elongated member. The actuator is adapted to be manipulated by an operator to urge the loops against the bias to a closed position permitting movement of the periphery toward the elongated member without interference from the loops.

18 Claims, 3 Drawing Sheets

EMBOLI FILTER

I. BACKGROUND OF THE INVENTION

1. Field of the Invention

This invention pertains to a medical apparatus for passage into a body lumen of a patient. More particularly, this invention pertains to an emboli filter for deployment in a patient's body lumen to capture emboli entrained in fluid flowing through the lumen.

2. Description of the Prior Art

There are numerous medical procedures for introducing tools into a patient's body lumen. For example, occlusion treatment tools (such as angioplasty balloon-tipped catheters, stents or ablation catheters) may be admitted into a lumen of an artery to treat an occluded site within the artery. A balloon tipped catheter may be expanded at the site to urge the occlusion against the walls of the artery to improve patency of the arterial lumen. A stent may be expanded at the site to maintain lumen patency. Alternatively, or in combination with other procedures, an ablation tool may be used to mechanical remove the occluding material.

The manipulation and use of tools within a lumen of a body passage may cause the release of emboli in the lumen. In arteries, such emboli become entrained within blood flow within the artery. Such emboli can contribute to morbidity. For example, emboli can be transported to the brain and contribute to cranial ischemia (stroke). In treating occlusions in coronary arteries, emboli may flow to occlude distal, micro-vessels contributing to myocardial ischemia.

In order to reduce morbidity associated with emboli, filters have been developed to capture emboli for removal from the lumen. An example of such a filter is shown in U.S. Pat. No. 5,695,519. Typically, such filters include a filter media carried on an elongated, flexible member. The filter media commonly has an open cell construction with a cell or mesh size of 50–300 micrometers ($\mu$m) to capture emboli while permitting fluid (e.g., blood) flow past the filter. The filter media is opened and closed in an umbrella-like fashion. In the open position, the filter media substantially fills the cross-section of the body lumen such that substantially all emboli-laden fluid flow must pass through the filter media. When closed, the filter media captures the emboli and the filter is reduced in size to pass through the lumen for removal.

Emboli filters should be easy to use and highly flexible to pass through narrow vasculature. The filters should open in a manner atraumatic to the vessel. The filter should open in a manner to accommodate a non-circular cross-section while covering as much as possible of the cross-sectional area of the vessel. Such a filter need not abut the wall of the vessel since fluid flow at the wall is turbulent and emboli-laden flow is spaced from the wall. Preferably the filter media is highly flexible and the filter design permits a long filter to enlarge filter volume.

II. SUMMARY OF THE INVENTION

An emboli filter is disclosed for deployment in a body lumen to capture emboli entrained in a fluid flowing through the lumen. The filter includes a flexible elongated member sized to be passed through the lumen. A filter media is carried on and substantially surrounds the elongated member. The filter media has a first end secured to the elongated member adjacent the distal end. A second end of the filter media has a periphery movable radially toward and away from the elongated member. Opposing internal surfaces of the filter media define a volume into which emboli may flow through the second end when the periphery is moved away from the elongated member. The emboli are trapped within the volume when the periphery is radially moved toward the elongated member. An actuator moves the periphery radially toward and away from the elongated member. The actuator includes a plurality of elastic loops. The loops are biased to an open loop configuration with the loops urging the periphery radially away from the elongated member. The actuator is adapted to be manipulated by an operator to urge the loops against the bias to a closed position permitting movement of the periphery radially toward the elongated member without interference from the loops.

III. BRIEF DESCRIPTION OF THE DRAWINGS

IV. DESCRIPTION OF THE PREFERRED EMBODIMENT

Figure 1:
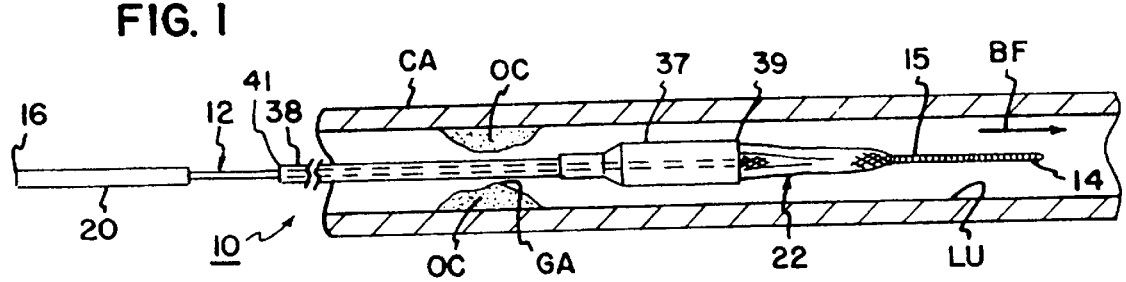
FIG. 1 is a side plan schematic view of an emboli filter according to the present invention being advanced through an artery with a distal end of the filter advanced past an occlusion.

With reference to the various drawing figures a description of a preferred embodiment of the present invention will now be provided. In the drawings, similar elements are numbered similarly throughout. In alternate embodiments, similar elements are similarly numbered with the addition of a distinguishing apostrophe to distinguish embodiments. Unless modified, such similar elements need not be described more than once. While the present invention could be used in a wide variety of body lumens (with the apparatus of the invention sized with respect to such lumens), the preferred embodiment will be described with reference to an emboli filter for use in a carotid artery.

With initial reference to FIGS. 1–5, an emboli filter 10 is shown deployed in a carotid artery CA having an internal lumen LU partially blocked by an occlusion OC. Blood flow is in the direction of arrow BF in FIG. 1. In FIG. 1, the occlusion OC is shown only partially blocking the lumen LU such that blood flows through lumen LU and through the gap GA of the occlusion OC.

The filter 10 includes a flexible, elongated member 12 having a distal end 14 and a proximal end 16. In the embodiment of FIGS. 1–5, the elongated member 12 is shown as a solid wire/mandrel. Of course, the elongated member 12 could also be a tube. A flexible, hollow tube 38 is mounted over the elongated member 12. The hollow tube 38 is adapted to slide longitudinally relative to the elongated member. An enlarged collar 37 forms a distal end 39 of the hollow tube 38. A proximal end 41 of the hollow tube 38 is preferably positioned adjacent to the proximal end 16 of the elongated member 12. In certain embodiments, handles can be attached to one or both of the proximal ends 16 and 41 for allowing a physician to better manipulate the filter 10. For example, a handle 20 is shown attached to the proximal end 16 of the elongated member 12.

The filter 10 also includes a filter media 22 connected to the elongated member 12 adjacent the distal end 14. In a deployed state (shown in FIG. 2), the filter media 22 has a conical shape coaxial with the elongated member 12. A closed conical tip 24 is secured to the elongated member 12. Proximal to conical tip 24, the filter media 22 has a periphery conical base 26.

Figure 2:
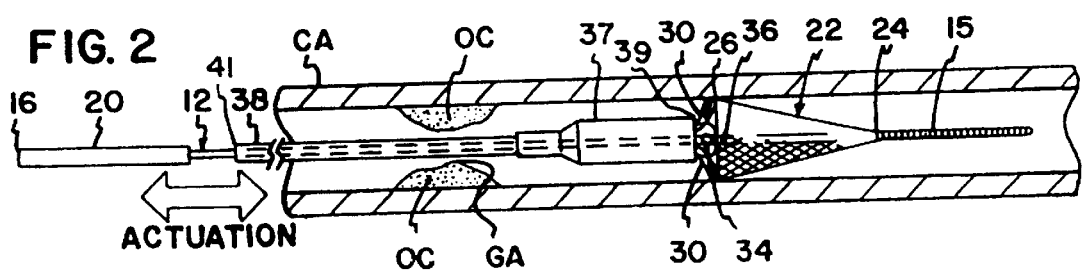
FIG. 2 is the view of FIG. 1 with the filter media shown in an open position to trap emboli.
Figure 3:
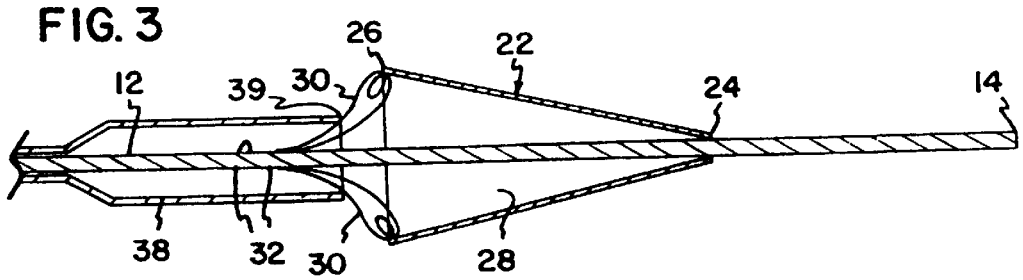
FIG. 3 is a side sectional view of a portion of the filter of FIG. 2.

Opposing surfaces of the filter media 22 define an internal volume 28 (FIG. 3). When the filter media 22 is in the open position (FIGS. 2, 3, 4 and 7), the periphery 26 is spaced from the elongated member 12. Therefore, blood laden with emboli can flow into the volume 28. The filter media 22 is porous or mesh construction such that blood flows through the filter media 22 with emboli being trapped with volume 28. After a therapy period, the filter media 22 is moved to a closed position (FIG. 5), with the periphery 26 drawn toward the elongated member 12 such that the emboli are captured in the closed volume 28.

Figure 4:
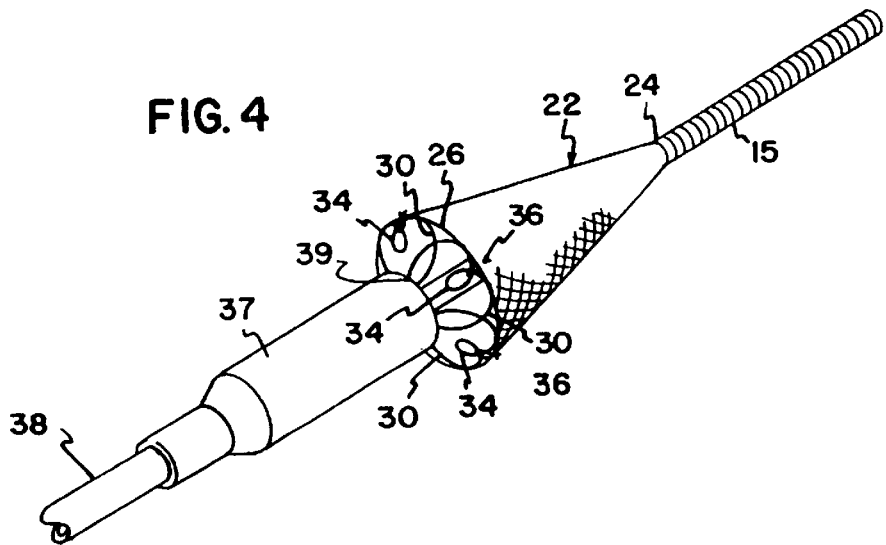
FIG. 4 is a rear and side perspective view of filter media and loop actuator according to the present invention.
Figure 5:
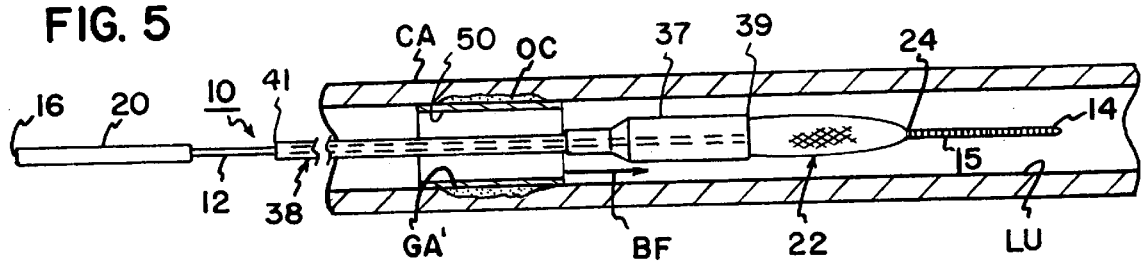
FIG. 5 is the view of FIG. 2 with the filter media closed to capture trapped emboli and with the filter reduced in size to be retracted from the artery.

The filter media 22 is flaccid and is held open by loops 30. Each of loops 30 is preferably identical. Three loops 30 are shown in FIGS. 2–4. More or fewer could be used. The loops 30 are formed of flexible resilient material. A suitable material may be nitinol (a well-known nickel-titanium alloy) or other metal or polymer. Ends 32 (FIG. 3) of the loops 30 are secured to the elongated member 12 with the loops 30 circumferentially spaced about the elongated member 12.

The loops 30 present a cloverleaf-shape such that the loops 30 have a secondary loop 34 at the top of each loop 30. The secondary loops 34 are a convenient attachment location for securing the loops 30 to the periphery 26 by sutures 36 or any other suitable fastening or adhering means. The cloverleaf-shape also provides a good balance of radial force against the artery CA.

The loops 30 are resiliently biased to open radially outwardly such that the loops are open in a plane perpendicular to the elongated member 12 when the loops 30 are in an open configuration. Each loop 30 is resiliently flexible independent of a remainder of the loops 30. Therefore, in an open configuration, the loops 30 can readily accommodate a non-circular interior diameter.

The loops 30 are movable against their bias to a closed configuration with the loops against the elongated member 12. When so moved, the loops 30 draw the periphery 26 toward the elongated member 12 to the closed position of FIGS. 1 and 5. When in the closed position of FIGS. 1 and 5, the periphery 26 of the filter media 22 is housed or contained within the collar 37. Thus, the collar 37 prevents the periphery 26 from expanding radially outward. The filter media 22 is opened and closed by longitudinally sliding the elongated member 12 and the tube 38 relative to one another. For example, when the tube 38 is held stationary while the elongated member is pulled proximally, the collar 37 urges the loops 30 against their bias from the open loop configuration toward the closed loop configuration. By contrast, the periphery 26 of the filter media 22 can be released from the collar 37 by holding the tube 38 stationary while pushing the elongated member in a distal direction.

In the closed state (FIGS. 1 and 5), the emboli filter 10 is sized to pass through gap GA to position the filter media 22 distal to an obstruction OC. Typically, the filter 10 will be positioned by inserting the distal tip 14 in a blood vessel through an incision, and then by manipulating the proximal end 16 to advance the tip 14 through the vasculature to the occlusion OC. Preferably, during the insertion process, the outer tube 38 and the elongated member 12 are moved together as one unit. Once the filter media 22 is positioned distal to the obstruction OC, the physician pushes the elongated member 12 distally relative to the collar to release loops 30 and open the filter media 22 (FIG. 2). Though desirable, the periphery 26 of the filter media 22 need not fully seat against the interior wall of the carotid artery CA. Fluid flow at the wall is turbulent and most emboli are carried in blood flow closer to the center of the lumen LU. Preferably, a distal portion 15 of the elongated member 12 is highly flexible to avoid trauma as the filter 10 is advanced.

After the filter media 22 is opened, the tube 38 can be removed from the elongated member 12 and a balloon angioplasty device can be slid over the member 12 and used to compress the occlusion OC against the lumen wall to provide an enlarged gap GA'. Thereafter, a stent 50 can be used to maintain the enlarged gap GA'. Such treatment may release emboli which are captured in the filter volume 28 while blood is permitted to pass through the filter media 22. When the therapy is complete, the tube 38 is re-inserted over the elongated member 12, and the elongated member 12 is pulled proximally relative to the collar 37 of the tube 38 to close the filter media 22. By closing the filter media 22, emboli are captured in the closed volume 28 and the size of the filter 22 is reduced so it can be pulled through the enlarged gap GA' (FIG. 5) and out of the carotid artery CA.

As described above, the filter media 22 is opened and closed by moving elongated member 12 distally and proximally relative to the tube 38 (and the attached collar 37). Alternatively, the filter media can be opened and closed by moving the tube 38 distally and proximally, respectively, relative to the elongated member 12. Further, the tube 38 and the elongated member 12 can also be concurrently moved in opposite directions to open and close the filter media 22.

Figure 6:
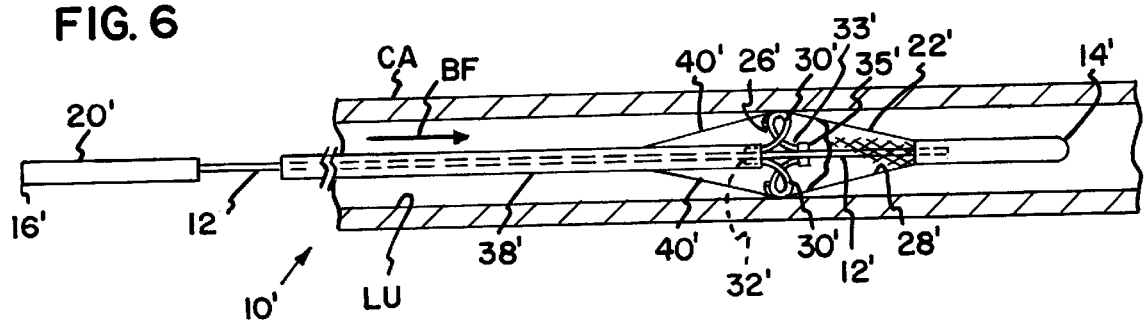
FIG. 6 is a side plan schematic view of an alternative embodiment of an emboli filter according to the present invention with a filter media shown in an open position to trap emboli.

FIG. 6 shows an alternative embodiment 10' having loops 30' that are not cloverleaf-shaped. Instead, the loops 30' have proximal ends 32' and distal ends 33'. The distal ends 33' are secured to an elongated member 12' by an attachment hub 35'. The proximal ends 32' are attached to an outer tube 38'. Flexible tie strings 40' are secured to a periphery 26' of a filter media 22', and also to the tube 38'.

As tube 38' is moved proximally relative to the elongated member 12', the tube 38' urges the loops 30' to a closed configuration and ties 40' simultaneously pull on the periphery 26' to urge the filter media 22' to be closed. Distal movement of elongated member 12' relative to the tube 38' results in the loops 30' being in the open configuration of FIG. 6 with the filter open. Again, as in the previous embodiment, the loops 30' present an open volume 28' perpendicular to the elongated member 12' so as not to interfere with blood flow. As shown in FIG. 6, the elongated member 12' has a proximal end 16' and an enlarged distal tip 14'.

Figure 7:
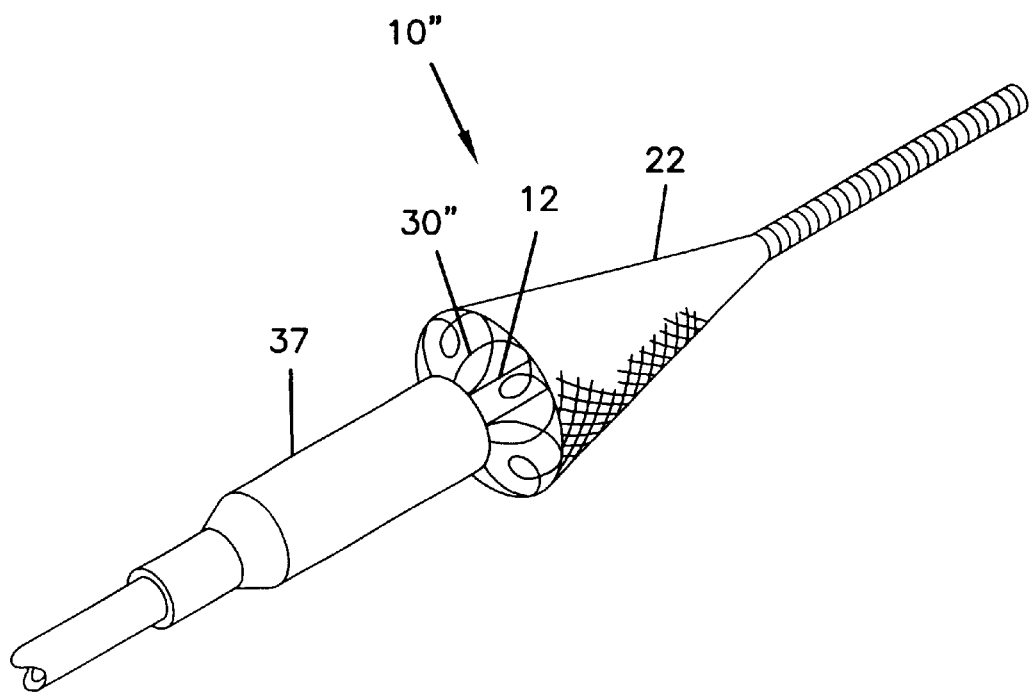
FIG. 7 is a perspective view of another emboli filter constructed in accordance with the principles of the present invention.

FIG. 7 shows another emboli filter 10" constructed in accordance with the principles of the present invention. The filter 10" has the same construction as the filter 10 of FIGS. 1–5, except the loops 30 have been replaced with loops 30" that do not include secondary loops 34. The loops 30 interconnect an outer filter media 22 to an elongated member 12. A collar 37 (i.e., a sheath) is provided for retracting or collapsing the filter media 22. It will be appreciated that the loops 30" serve the same function as the loops 30, and the filter 10" operates in the same manner previously described with respect to the filter 10 of FIGS. 1–5.

From the foregoing, the present invention has been disclosed in a preferred embodiment. It is intended that modifications and equivalents of the disclosed concepts, such as those which readily occur to one of skill in the art shall be included within the scope of the claims appended hereto.

What is claimed is:

1. An emboli filter for deployment in a body lumen, said emboli filter comprising:
   a flexible elongated member sized to be passed through said lumen, said elongated member having a distal end and a proximal end;
   a filter media carried on and substantially surrounding said elongated member, said filter media having a first end and a second end, said first end secured to said elongated member adjacent said distal end, said second end having a periphery movable toward and away from said elongated member, opposing internal surfaces of said filter media defining a volume into which emboli may flow through said second end when said periphery is moved away from said elongated member, said emboli trapped within said volume when said periphery is moved toward said elongated member;
   an actuator for selectively moving said periphery toward and away from said elongated member, said actuator including a plurality of elastic loops, each of said loops having a first end and a second end, each of said first and second ends being attached to said elongated member, said first end being attached adjacent to said second end, said loops biased to an open loop configuration with said loops urging said periphery away from said elongated member, said actuator adapted to be manipulated by an operator to urge said loops against said bias to a closed position permitting movement of said periphery toward said elongated member without interference from said loops.

2. A filter according to claim 1 wherein each of said loops is attached to said periphery at individual ones of a plurality of attachment locations spaced apart on said periphery and with said attachment locations drawing said periphery toward said elongated member as said loops are moved to said closed position.

3. A filter according to claim 1 wherein said loops are open in a plane substantially perpendicular to said elongated member when said loops are biased to said open loop configuration.

4. A filter according to claim 1 wherein each of said loops is resiliently flexible independent of a remainder of said loops.

5. A filter according to claim 1 wherein said filter media is substantially flaccid and held open only by said loops in said open loop configuration.

6. A filter according to claim 2 wherein each of said loops includes a secondary loop at said attachment locations.

7. A filter according to claim 1 wherein said actuator includes a movable collar movable axially relative to said elongated member, relative movement of said collar toward said distal end causing said loops to be urged to said closed position.

8. A filter according to claim 1 wherein said elongated member is hollow throughout a length of said elongated member.

9. A filter according to claim 1 wherein said periphery is overlying said loops and said periphery is secured to said elongated member proximal to said loops by a flexible tie.

10. A filter according to claim 1, further comprising a tube mounted over the elongated member, the tube and the elongated member being longitudinally moveable relative to one another.

11. An emboli filter for deployment in a body lumen, said emboli filter comprising:
    a flexible elongated member sized to be passed through said lumen, said elongated member having a distal end and a proximal end;
    a filter media carried on and substantially surrounding said elongated member, said filter media having a first end and a second end, said first end secured to said elongated member adjacent said distal end, said second end having a periphery movable toward and away from said elongated member, opposing internal surfaces of said filter media defining a volume into which emboli may flow through said second end when said periphery is moved away from said elongated member, said emboli trapped within said volume when said periphery is moved toward said elongated member;
    an actuator for selectively moving said periphery toward and away from said elongated member, said actuator including a plurality of elastic loops, each of said loops having a first end, a second end, and a looped portion therebetween, said loops biased to an open loop configuration with said loops urging said periphery away from said elongated member, said actuator adapted to be manipulated by an operator to urge said loops against said bias to a closed position permitting movement of said periphery toward said elongated member without interference from said loops.

12. A filter according to claim 11, further comprising a tube mounted over the elongated member, the tube and the elongated member being longitudinally moveable relative to one another.

13. A filter according to claim 12, wherein the first end of each of the elastic loops is connected to the tube and the second end of each of the elastic loops is connected to the elongated member.

14. A filter according to claim 13, further comprising tie members that connect the periphery of the filter media to the tube.

15. An emboli filter for deployment in a body lumen, said emboli filter comprising:
    a flexible elongated member sized to be passed through said lumen, said elongated member having a distal end and a proximal end;
    a filter media carried on and substantially surrounding said elongated member, said filter media having a first end and a second end, said first end secured to said elongated member adjacent said distal end, said second end having a periphery movable toward and away from said elongated member, opposing internal surfaces of said filter media defining a volume into which emboli may flow through said second end when said periphery is moved away from said elongated member, said emboli trapped within said volume when said periphery is moved toward said elongated member;
    an actuator for selectively moving said periphery toward and way from said elongated member, said actuator including a plurality of elastic loops, said loops biased to an open loop configuration with said loops urging said periphery away from said elongated member, said loops being attached to said periphery at individual ones of a plurality of attachment locations spaced apart on said periphery, said loops including a secondary loop at said attachment locations and with said attachment locations drawing said periphery toward said elongated member as said loops are moved to said closed position, said actuator adapted to be manipulated by an operator to urge said loops against said bias to a closed position permitting movement of said periphery toward said elongated member without interference from said loops.

16. An emboli filter for deployment in a body lumen, said emboli filter comprising:
- a flexible elongated member sized to be passed through said lumen, said elongated member having a distal end and a proximal end;
- a filter media carried on and substantially surrounding said elongated member, said filter media having a first end and a second end, said first end secured to said elongated member adjacent said distal end, said second end having a periphery movable toward and away from said elongated member, opposing internal surfaces of said filter media defining a volume into which emboli may flow through said second end when said periphery is moved away from said elongated member, said emboli trapped within said volume when said periphery is moved toward said elongated member;
- an actuator for selectively moving said periphery toward and away from said elongated member, said actuator including a plurality of elastic loops, each loop including a primary loop and a secondary loop, said loops biased to an open loop configuration with said primary loops urging said periphery away from said elongated member, said actuator adapted to be manipulated by an operator to urge said loops against said bias to a closed position permitting movement of said periphery toward said elongated member without interference from said loops.

17. A filter assembly according to claim 16, further comprising means for attaching the secondary loops to the filter media.

18. An emboli filter for deployment in a body lumen, said emboli filter comprising:
- a flexible elongated member sized to be passed through said lumen, said elongated member having a distal end and a proximal end;
- a filter media carried on and substantially surrounding said elongated member, said filter media having a first end and a second end, said first end secured to said elongated member adjacent said distal end, said second end having a periphery movable toward and away from said elongated member, opposing internal surfaces of said filter media defining a volume into which emboli may flow through said second end when said periphery is moved away from said elongated member, said emboli trapped within said volume when said periphery is moved toward said elongated member;

an actuator for selectively moving said periphery toward and away from said elongated member, said actuator including a plurality of elastic loops, each of said loops having a first end and a second end, said first and second ends being attached to said elongated member adjacent to said second end of said filter media, said loops biased to an open loop configuration with said loops urging said periphery away from said elongated member, said actuator adapted to be manipulated by an operator to urge said loops against said bias to a closed position permitting movement of said periphery toward said elongated member without interference from said loops.

* * * * *